US006932967B2

(12) United States Patent
Simon

(10) Patent No.: US 6,932,967 B2
(45) Date of Patent: Aug. 23, 2005

(54) HUMAN MEDICAL TREATMENT BY AEROSOL INHALATION OF IMMUNOGLOBULIN A

(76) Inventor: Michael R. Simon, 1925 Scottwood, Ann Arbor, MI (US) 48104

( * ) Notice: Subject to any disclaimer, the term of this patent is extended or adjusted under 35 U.S.C. 154(b) by 0 days.

(21) Appl. No.: 09/815,026

(22) Filed: Mar. 22, 2001

(65) Prior Publication Data

US 2002/0136695 A1 Sep. 26, 2002

(51) Int. Cl.$^7$ ..................... A61K 39/00; A61K 39/395; C07K 16/00; C12P 21/08
(52) U.S. Cl. ............................... 424/130.1; 424/178.1; 530/350; 530/389.1; 530/391.1
(58) Field of Search ........................... 424/130.1, 178.1, 424/134.1, 141.1, 142.1, 147.1, 193.1; 530/350, 389.1, 391.1

(56) References Cited

U.S. PATENT DOCUMENTS

| 4,482,483 | A | * | 11/1984 | Curry et al. |
| 4,695,068 | A | * | 9/1987 | Kawamoto et al. |
| 5,210,183 | A | * | 5/1993 | Lindahl et al. |
| 5,258,177 | A | * | 11/1993 | Uemura et al. |
| 5,670,626 | A | | 9/1997 | Chang |
| 5,808,000 | A | | 9/1998 | Mannhalter et al. |
| 6,019,968 | A | | 2/2000 | Platz et al. |
| 6,063,905 | A | * | 5/2000 | Capra et al. |
| 6,124,132 | A | | 9/2000 | Blake |
| 6,165,463 | A | * | 12/2000 | Platz et al. ............... 424/130.1 |

FOREIGN PATENT DOCUMENTS

| DE | 4122784 | 1/1993 |
| EP | 1 068 871 A1 | 1/2001 |

OTHER PUBLICATIONS

Rindisbacher et al, J Biol Chem 270(3): 14220–28; 1995.*
Zikan et al, Mol Immunol 23(5): 541–4, May 1986, Abstract.*
Jones et al, Biochim Biophys Acta 429(1): 265–74, Dec. 1998.*
Johansen et al, Eur J Immunol 29: 1701–1708, 1999.*
Boros et al, Immunologiae Hungaricae 17: 57–61, 1974.*
Lindh et al, Eur J Biochem 62(2): 263–70, 1976.*
Symersky et al, Molecular Immunol 37: 133–140, Feb.–Mar. 2000.*
Berzofsky, J.A., Berkower, I.J., Epstein, S.L., Monoclonal Antibodies in Chapter 12, Antigen–Antibody Interactions and Monoclonal Antibodies, pp. 455–465 in Fundamental Immunology, Third Edition, WE Paul (ed), Raven Press, NY 1993.
Cohn, E.J., Strong, L.E., Hughes, W.L., Jr., Mulford, D.J., Ashworth, J.N., Melin, M., Taylor, H.L., Preparation and Properties of Serum and Plasma Proteins IV. A System for the Separation into Fractions of the Protein and Lipoprotein Components of Biological Tissues and Fluids, J. Am Chem Soc. 1946; 68;459–475.

Corthesy, B., Recombinent Secretory IgA for Immune Intervention Against Mucosal Pathogens, Biochem Soc Trans. 1997, 25;471–475.
Crottet, P., Cottet, S., Corthesy, B., Expression, Purification and Biochemical Characterization of Recombinant Murine Secretory Component, A Novel Tool in Mucosal Immunology, Biochem J 1999, 341;299–306.
Fahy, J.V., Cockcroft, D.W., Boulet, L.P., Wong, H.H., Deschesnes, F., David, E.E., Ruppel, J., Su, J.Q., Adelman, D.C., Effect of Aerosolized Anti–IgE (E25) on Airway Responses to Inhaled Allergen in Asthmatic Subjects. Am J Respir Crit Care Med 1999, 160:1023–1027.
Fruchtman, M.H., Mauceri, A.A., Wigley, F.M., Waldman, R.H., Aerosol Administration of Human Gamma Globulin as Prophylaxis against Influenza Virus Challenge. Clin Med 1972 (Sep.), 79:17–20.
Giraudi, V., Riganti, C., Torales, M.R., Sedola, H., Gaddi, E., Upper Respiratory Infections in Children, Response to Endonasal Administration of IGA. Int J Prediatr Otorhinolarynol, 1997; 39:103–110.
Heikkinen, T., Ruohola, A., Ruuskanen, O., Waris, M., Uhari, M., Hammarstrom, L., Intranasally Administered Immunoglobulin for the Prevention of Rhinitis in Children; Pediatr Infect Dis J 1998; 17:367–372.
Hemmingsson, M., Hammarstrom, L., Nasal Administration of Immunoglobulin as Effective Prophylaxis Against Infections in Elite Cross–Country Skiers. Scand J Infect Dis 1993; 25:73–75.
Johansen, F–E., Norderhaug, I. N., Roe, M., Sandlie, I. and Brandtzaeg, P., Recombinant expression of polymeric IgA: incorporation of J chain and secretory component of human origin, Eur. J. Immunol. 1999; 29: 1701–1708.

(Continued)

Primary Examiner—Christina Chan
Assistant Examiner—Phuong Huynh
(74) Attorney, Agent, or Firm—Gifford, Krass, Groh, Sprinkle, Anderson & Citkowski, P.C.

(57) ABSTRACT

Pooled human plasma is processed by cold ethanol fractionation to produce purified immunoglobulin G antibodies for intravenous administration. Immunoglobulin A is an unwanted by-product since intravenous administration of immunoglobulin A-containing immunoglobulin G can cause life-threatening anaphylaxis in some people. The present invention is the aerosol administration, by metered dose inhaler or nebulizer, of by-product immunoglobulin A for the prevention or treatment of diseases including immunodeficiencies and infections. Antigen-specific monoclonal immunoglobulin A may be used. Immunoglobulin A from any of the aforementioned sources may then be coupled with recombinant J chain, and may then be additionally coupled with recombinant secretory component in order to render the immunoglobulin A more physiologically active. Immunoglobulin A, with or without J chain and secretory component, is then administered by aerosol inhalation.

9 Claims, No Drawings

OTHER PUBLICATIONS

Kohler, G., Milstein, C., Continuous Cultures of Fused Cells Secreting Antibody of Predetermined Specificity, Nature 1975;256;495–497.

Lindberg, K., Berglund, B., Effect of Treatment with Nasal IgA on the Incidence of Infectious Disease in World–Class Canoeists. Int J Sports Med 1996; 17:235–238.

Lullau, E., Heyse, S., Vogel, H., Marison, I., von Stockar, U., Kraehanbuhl, J–P., Corthesy, B., Antigen Binding Properties of Purified Immunoglulin A Antibodies, J Biol Chem 1996; 271:16300–16309.

Mazanec, M.B., Lamm, M.E., Lyn, D., Portner, A., Nedrud, J.G., Comparison of IgA versus IgG Monoclonal Antibodies for Passive Immunization of the Murine Respiratory Tract. Virus Res 1992; 23:1–12.

Mazanec, M.B., Nedrud, J.G., Lamm, M.E., Immunoglobulin A Monoclonal Antibodies Protect against Sendai Virus. J. Virol. 1987; 61:2624–2626.

Oncley, J.L., Melin, M., Richert, D.A., Cameron, J.W., Gross, P.M., Jr., The Separation of the Antibodies, Isoagglutinins, Prothrombin, Plasminogen and $\beta$1–Lipoprotein into Subfractions of Human Plasma. J Am Chem Soc 1949;71:541–550.

Outlaw, M.C., Dimmock, N.J., Mechanisms of Neutralization of Influenza Virus on mouse Tracheal Ephithelial Cells by Mouse Monoclonal Polymeric IgA and Polyclonal IgM directed against the Viral Haemaglutinin. J Gen Virol 1990;71:69–76.

Rimensberger, P.C., Schaad, U.B., Clinical Experience with Aerosolized Immunoglobulin Treatment of Respiratory Syncytial Virus Infection in Infants. Pediatr Infect Dis J 1994;13:328–330.

Rindisbacher, L., Cottet, S., Wittek, R., Kraehenbuhl, J.P., Corthesy, B., Production of Human Secretory Component with Dimeric IgA Binding Capacity Using Viral Expression Systems. J Biol Chem 1995;270:14220–14228.

Strong, L.E., Blood Fractionation, pp. 576–602 in vol. 3, Kirk–Othmer Encyclopedia of Chemical Technology. Second Edition, H.F. Mark, J.J. McKetta, D.F. Othmer (eds), Interscience Publishers, NY 1963.

Symersky, J., Novak, J., McPherson, D.T. DeLucas, L., Mestecky, J., Expression of the Recombinant Human Immunoglobulin J Chain in *Escheria coli*. Mol Immunol 2000, 37:133–140.

Tamara, S., Funato, H., Hirabayashi, K., Kikuta, K., Suzuki, Y., Nagamine, T., Aizawa, C., Kurata, T., Cross–Protection against Influenza A Virus Infection by Passively Transferred Respiratory Tract IgA Antibodies to different Haemagglutinin Molecules. Eur J Immunol 1991;21:1337–1344.

Tamura, S., Funato, H., Hirabayashi, K., Kikuta, K., Suzuki, Y., Nagamine, T., Aizawa, C., Nakagawa, M., Kurata, T., Functional Role of Respiratory Tract Haemagglutinin–Specific IgA Antibodies in Protection against Influenza. Vaccine 1990;8:479–485.

Taylor, H. P., Dimmock, N.J., Mechanism of Neutralization of Influenza Virus by Secretory IgA is Different from that of Monomeric IgA or IgG. J Exp Med 1985;161:198–209.

Weltzin, R., Hsu, S.A., Mittler, E.S., Georgakopoulas, K., Monath, T.P., Intranasal Monoclonal Immunoglobulin A against Respiratory Synctial Virus Protects against Upper and Lower Respiratory Tract Infections in Mice. Antimicrob Agents Chemother. 1994;38:2785–2791.

Weltzin, R., Traina–Dorge, V., Soike, K., Zhang, J.Y., Mack, P., Soman, G., Drabik, G., Monath, T.P., Intranasal Monoclonal IgA Antibody against Respiratory Syncytial Virus Protects Rhesus Monkeys against Upper and Lower Respiratory Tract Infection. J Infect Dis 1996;174:256–261.

Wolff, R.K., Niven, R.W., Generation of Aerosolized Drugs. J Aerosol Med 1994;7:89–106.

Bezares et al. "Prevencion de infecctiones en pacientes con sindromes linfoproliferativos y mieloma por nebulizacion de un concentrado de IgA" Sangre 1997; 42(3):219–222.

Sanchez Avaios et al. "Nebulizaciones con IgA humana en pacientes con hipogammaglobullnemia e infecciones de las vias aeras secundararias a enfermedades linfoproliferativas" Medicina (Buenos Aires) 1995; 55(6):727–729.

Leibel et al. "Method for the isolation of biologically active monomeric immunoglobulin A from a plasma fraction" Journal of chromatography B, 678 (1996) 173–180.

Document bibliography and abstract, Patent WO 0103727.

Document bibliography and abstract, Patent CS242310.

* cited by examiner

HUMAN MEDICAL TREATMENT BY AEROSOL INHALATION OF IMMUNOGLOBULIN A

FIELD OF THE INVENTION

The present invention relates to human medical treatment by aerosol inhalation of immunoglobulin (Ig) A. More specifically the invention relates to treatment of immunodeficiencies and viral or bacterial infections of the lower respiratory tract by administering doses of IgA or an antibody composition rich in immunoglobulin A.

BACKGROUND OF THE INVENTION

Immunoglobulins (also called antibodies) are a group of structurally related proteins composed of heavy and light chains. These proteins are categorized as IgM, IgG, IgD, IgE, and IgA depending upon the characteristics of the constant regions of their heavy chains (designated $\mu$, $\gamma$, $\delta$, $\epsilon$, and $\alpha$, respectively). The variable regions of the heavy chains along with the variable regions of the light chains determine the molecular (antibody) specificity of the complete molecule. These molecules are secreted by B lymphocytes in response to signals from other components of the immune system. Their function is to prevent and combat infection by viruses and bacteria.

Purified IgG from pooled human plasma is administered intravenously in humans to treat a variety of conditions. In the purification, a fraction rich in IgA is considered an unwanted by-product, since intravenous administration of IgA containing immunoglobulin can cause life threatening anaphylaxis in some patents.

IgA on mucosal surfaces is produced locally and not derived from circulating IgA. IgA is one of the y globulins on the basis of its electrophoretic mobility. IgA is composed of two a heavy chains and two light chains. It may be monomeric (i.e. a single molecule), dimeric (composed of two molecules) or trimeric (composed of three molecules). IgA monomers are joined together as dimers at the constant regions of their heavy chains by a J chain. IgA is secreted as one of two subclasses, IgA1 and IgA2. IgA1 predominates in the circulating blood wherein most of it occurs as a monomer. Most IgA on mucosal surfaces, such as the surfaces of the trachea, bronchi, and bronchioles in the lungs, occurs as dimers or trimers joined by J chains. IgA dimers and trimers have an increased ability to bind to and agglutinate target molecules (antigens). Agglutinated antigens are more readily phagocytosed and thereby eliminated. In addition, IgA dimers and trimers, because of the presence of their J chains, have the ability to attach to secretory component. Such molecules then have increased resistance to proteolytic enzymatic degradation. Human J chains (Symerski, etal., Mol Immunol 2000; 37:133–140) and murine secretory component (Crottet, et al., Biochem J 1999; 341:299–306) have been produced by genetic recombinant biological techniques. Recombinant expression of polymeric IgA with the incorporation of J chain and secretory component of human origin has been accomplished (Johansen, et al., Eur J Immunol 1999; 29:1701–1708)

IgA can attach to the cell surface of phagocytic leukocytes and thereby facilitate antibody-dependent cell-mediated killing of microorganisms. It also interacts with lactoperoxidase and lactoferrin which enhances the latter's antibacterial actions. Monomeric IgA interferes with influenza virus replication (Taylor, et al., J Exp Med 1985; 161:198–209) and polymeric IgA interferes with influenza binding to and entry into target cells (Taylor, et al. J Exp Med 1985; 161:198–209; Outlaw and Dimmock, J Gen Virol 1990; 71:69–76).

Exogenous IgA has been topically applied to the nose in both animals and humans for the purpose of preventing and treating disease. In mice, nasal application of exogenous IgA has been demonstrated to be efficacious in protecting animals from influenza (Tamura, et al., Vaccine 1990; 8:479–485, Tamura, etal., Eur J Immunol 1991; 21:1337–1344), Sendai virus (Mazanec, et al., J Virol 1987; 61:2624–2626, Mazanec, etal., Virus Res 1992; 23:1–12) and respiratory syncytial virus (Weltzin, et al, Antimicrob Agents Chemother 1994; 38:2785–2791) challenge. Intranasal monoclonal IgA also protects rhesus monkeys against respiratory syncytial virus infection (Weltzin, et al., J Infect Dis 1996; 174:256–261). In humans, nasal administration of approximately 70% IgA/30%IgG resulted in decreased frequency of upper respiratory tract infections in elite skiers (Hemmingsson and Hammarstrom, Scand J Infect Dis 1993; 25:73–75), and in children (Giraudi, et a., Int J Pediatr Otorhinolarynol 1997; 39:103–110, Heikkinen, et al., Pediatr Infect Dis J 1998; 17:367–372) but not in elite canoeists (Lindberg and Berglund, Int J Sports Med 1996; 17:2335–238).

Aerosol administration of human $\gamma$ globulin (Fruchtman, et al., Clin Med 1972 (Sept);79:17–20), pooled human IgG (Rimensberger and Schaad, Pediatr Infect Dis J 1994; 13:328–330) and murine recombinant humanized IgG (Fahy, et al., Am J Respir Crit Care Med 1999; 160:1023–1027) demonstrated that there are no adverse effects from the aerosol inhalation of human $\gamma$ globulin or human or humanized IgG.

Individuals suffering from hypogammaglobulinemia or with bronchial infections from other sources have been treated by a number of means, none of which has proven to be completely satisfactory. On the one hand, such patients have been treated by administration of antibiotics. However, antibiotics treatment is not completely effective in preventing infection in patients with immunoglobulin deficiency or whose immune systems are otherwise compromised. Another method of treating such patients has been intravenous infusion of immunoglobulin. The immunoglobulin administered by intravenous infusion does not contain the secretory piece. As a result, the infused immunoglobulin may not reach the mucosal surface of the bronchial tree. In addition, intravenous infusion of immunoglobulin is usually administered by trained medical personnel and can be associated with systemic reactions. There is thus a need for methods which can be used to deliver IgA to the bronchial mucosal surface. It would be advantageous if such treatment could be administered by the patient without the need for intervention by trained medical personnel. It would further be desirable to make use of unwanted by-products resulting from the preparation of purified immunoglobulin G from pooled human plasma. The present invention provides these advantages and others as will be apparent to one with skill in the art from the disclosure that follows.

SUMMARY OF THE INVENTION

The invention provides a method for medical treatment of humans that involves pulmonary administration by inhalation of an immunoglobulin (Ig) A composition. In one embodiment, the IgA is prepared as a by-product from pooled human plasma and is derived from a Cohn fraction component enriched in IgA. In another embodiment, the IgA composition contains a monoclonal antigen-specific IgA. In a preferred embodiment, the IgA component is further combined with recombinant human J chains and recombinant secretory component to produce a more physiologically effective composition. Conditions treatable by pulmonary administration of such compositions include immunodeficient diseases, immune suppression, bacterial infections, and viral infections.

DETAILED DESCRIPTION OF THE PREFERRED EMBODIMENTS

The following description of the preferred embodiment(s) is merely exemplary in nature and is in no way intended to limit the invention, its application, or uses.

In one embodiment, the invention provides a method for medical treatment of humans comprising the step of administering by inhalation an aerosol composition. The aerosol composition contains an IgA component which can be derived from a number of sources. The aerosol composition contains an IgA component which can be derived from a number of sources. The by-product is obtained from pooled human plasma following Cohn cold ethanol fractionation to produce fraction III precipitate as performed by those of skill in the art of protein separation. IgA by-product is further purified by adsorption onto a ion exchange medium in neutral or slightly acidic conditions as performed by those of skill in the art of protein purification.

A more detailed description of isolation of an IgA component as a by-product from pooled human plasma or hyperimmune pooled human plasma is as follows. Ethanol fractionation of pooled human plasma is a well known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. This is because some individuals undergo an anaphylactic-like reaction if treated with intravenous IgG that contains IgA as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA is generally discarded as an unwanted by-product. According to the invention, this unwanted IgA following ion exchange adsorption purification, is further treated by incubation with immobilized hydrolases to inactivate viruses and vasoactive substances. Such treatment has been proven to eliminate many viruses tested including HIV, Sindbis, and vaccinia. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn, et al., J Am Chem Soc 1946; 68:459–475, Oncley, et al, J Am Chem Soc 1949; 71:541–550, and in most detail in pages 576–602, Kirk-Othmer Encyclopedia of Chemical Technology, Vol 3, second edition (1963), the disclosure of which is hereby expressly incorporated by reference.

In a preferred embodiment, the compositions of the invention contain, in addition to the IgA component, one or more further components selected from the group consisting of recombinant human J chains, recombinant secretory component, and combinations thereof. The production of human J chains by genetically recombinant biological techniques is disclosed in Symerski, et al., Mol Immunol 2000; 37:133–140, the disclosure of which is hereby incorporated by reference. Human secretory component can be produced by recombinant techniques as described in Croftet, et al, Biochem J 1999; 341:299–306, disclosure of which is hereby incorporated by reference. In a preferred embodiment the IgA may be coupled to recombinant J chains by disulfide bonding which is accomplished in mildly oxidizing conditions. The resulting IgA-J chain conjugates are purified. IgA-J chain conjugates may then be further coupled to recombinant secretory component. In a preferred embodiment, the coupling is accomplished by forming disulfide bonds under mildly oxidizing conditions. IgA containing both J chain and secretory component is again purified by ion-exchange and size exclusion chromatography and/or ultrafiltration as described in Lullau, et al., J. Biol Chem 1996; 271:16300–16309, Corthesy, Biochem Soc Trans 1997; 25:471–475, and Crottet, et al., Biochem J 1999; 341:299–306, as performed by those of skill in the art of protein purification, the disclosures of which are hereby incorporated by reference. While recombinant expression of IgA with the incorporation of J chain and secretory component has been accomplished, hybridoma production of IgA may not include incorporated J chains and secretory component. According to the invention, the recombinant J chains, recombinant secretory component, or mixtures of them may be combined with the monoclonal IgA after production of the IgA by hybridoma techniques. Such IgA may be coupled to recombinant J chains and secretory component as described above. Purified IgA containing J chain and secretory components can be stabilized for example by the addition of human serum albumin to a final concentration of 5%. The presence of the human J chains and secretory component in the compositions of the invention leads to inhaled doses of immunoglobulin which are more physiologically effective than compositions without such components.

In another embodiment, an IgA containing component is isolated as a by-product from hyperimmune pooled human plasma for coupling with J chain and secretory component. Hyperimmune pooled human plasma is obtained from donors who have been immunized against a specific disease.

In another embodiment, the IgA component can be prepared by hybridoma techniques to provide antigen-specific IgA. Hybridoma techniques are described originally in Kohler and Milstein, Nature 1975; 256:495–497 with more recent advances summarized in Berzofsky et al., Fundamental Immunology, Third Edition, 1993, pp 455–462, the disclosures of which are hereby incorporated by reference. Hybridoma production involves the fusion of an immortalized immunoglobulin-producing myeloma cell with an antibodyproducing cell from an immunized individual. The product is an immortalized cell culture which produces the specific antibody against the antigen that the donor individual is immune to. For example, a mouse monoclonal IgA antibody has been prepared against respiratory syncytial virus F glycoprotein as described in Weltzin, et al., J Infect Dis 1996; 174:256–261 and Weltzin, eta., Antimicrob Agents Chemother 1994; 38:2785–2791.

The compositions of the invention for pulmonary delivery of aerosol compositions generally contain in addition to the IgA component and optional J chains and secretory component known pharmaceutical excipients and buffering agents. Non-limiting examples of such excipients include proteins as for example, human serum albumin and recombinant human albumin. Other pharmaceutical excipients include carbohydrates, sugars, and alditols. Non-limiting examples of suitable carbohydrates include sucrose, lactose, raffinose, and trehalose. Suitable alditols include mannitol, and pyranosyl sorbitol. Polymeric excipients include polyvinylpyrolidone, Ficolls, soluble hydroxyethyl starch, and the like of suitable molecular weight. Non-limiting examples of suitable buffering agents include salts prepared from organic acids such as citric acid, glycine, tartaric acid, lactic acid, and the like. Other useful excipients include surfactants and chelating agents. The compositions of the invention are readily aerosolized and rapidly deposited in the lungs of a host. Doses are formulated from the compositions of the invention by combining the IgA component with or without human J chain and secretory component, and pharmaceutical excipients so as to contain an effective dose of the active ingredient. A typical dose would include about 5 milligrams of active material. The dose amount may be adjusted up or down as required to meet the treatment needs of an individual, or to provide for ease and convenience in administering the dose.

The compositions of the invention can be administered by nebulization or by metered dose inhalers. Nebulizers and metered dose inhalers are well know in the art and are described for example, in Wolff and Niven, J Aerosol Med 1994; 7:89–106.

Diseases and conditions for which aerosol pulmonary administration of the compositions of the invention is to be used therapeutically or prophylactically include, but are not limited to: common variable immunodeficiency, IgA deficiency, human immunodeficiency virus (HIV) infection, lower respiratory tract infection with influenza, lower respiratory tract infection with respiratory syncytial virus, lower respiratory tract infection with rhinovirus, lower respiratory tract infection with adenovirus, chronic lymphocytic leukemia, multiple myeloma, macroglobulinemia, chronic bronchitis, bronchiectasis, asthma, immune suppression associated with bone marrow transplantation, immune suppression associated with cyclophosphamide administration, immune suppression associated with azathiaprine administration, immune suppression associated with methotrexate administration, immune suppression associated with chlorambucil administration, immune suppression associated with nitrogen mustard administration, immune suppression associated with 6-mercaptopurine administration, immune suppression associated with thioguanine administration, severe combined immunodeficiency, adenosine deaminase deficiency, major histocompatibility class I (Bare leukocyte syndrome) and class II deficiencies, purine nucleoside phosphorylase deficiency, DiGeorge Syndrome, transient hypogammaglobulinemia of infancy, X-linked agammaglobulinemia, X-linked agammaglobulinemia with growth hormone deficiency, transcobalamin II deficiency, immunodeficiency with thymoma, immunodeficiency with hereditary defective response to Epstein Barr virus, immunoglobulin deficiency with increased IgM, K chain deficiency, ataxiatelangiectasia, and immunodeficiency with partial albinism.

As used here, the term therapeutic treatment means that the patient being administered a dose of a composition of the invention has been diagnosed as having the condition to be treated. Prophylactic treatment means that the patient is being treated to prevent infection. Such treatment is often indicated where a patient is at risk for lower respiratory tract infection.

EXAMPLE

Polyclonal IgA is obtained from pooled human plasma following Cohn cold ethanol fractionation to produce fraction III precipitate. IgA is further purified by adsorption onto an ion exchange medium in neutral or slightly acidic conditions. Alternatively, monoclonal IgA is obtained from an IgA-producing hybridoma. The IgA is then coupled to recombinant J chains by disulfide bonding which is accomplished in mildly oxidizing conditions. The molar ratio of IgA to J chain is 2:1 or 3:1. IgA-J chain conjugates are purified. IgA-J chain conjugates may then be further coupled to recombinant secretory component again by disulfide bonding in mildly oxidizing conditions, preferably at a molar ratio of secretory componant to IgA-J chain conjugates of 1:1. IgA containing both J chain and secretory component is again purified. Purified IgA containing J chain and secretory componant is stabilized by the addition of human serum albumin to a final concentration of 5%. The final solution, adjusted to a therapeutic dose of 5 mg IgA, is then placed in a nebulizer for self-administration.

The description of the invention is merely exemplary in nature and, thus, variations that do not depart from the gist of the invention are intended to be within the scope of the invention. Such variations are not to be regarded as a departure from the spirit and scope of the invention.

I claim:

1. A composition for aerosol administration by inhalation, comprising polyclonal monomeric IgA having a recombinant J chain and a recombinant secretory component in a molar ratio of the IgA to the J chain of 2:1 and a molar ratio of an IgA-J chain conjugate to the secretory component of 1:1, wherein the J chain and secretory component are sequentially combined with the IgA, and wherein the IgA comprises a by-product of cold ethanol fractionation of pooled plasma derived from more than one human individual, wherein the by-product is prepared by:
   providing pooled human plasma;
   fractionating the pooled human plasma to produce an IgA rich fraction;
   adsorbing the IgA rich fraction onto an ion exchange medium to form a bound portion of the IgA;
   recovering the bound portion of the IgA;
   subjecting the recovered bound portion of the IgA to antiviral treatment; and
   sterilizing the resulting product.

2. The composition according to claim 1, wherein the pooled human plasma is derived from specifically immunized donors.

3. An aerosol composition comprising purified polyclonal monomeric IgA conjugated to:

a recombinant J chain and recombinant secretory component in a molar ratio of the IgA to the J chain of 2:1 and a molar ratio of an IgA-J chain conjugate to the secretory component of 1:1, wherein the J chain and secretory components are sequentially combined with the IgA; and a pharmaceutically acceptable solvent suitable for forming an aerosol.

4. The composition of claim 3 wherein the recombinant J chain is humanized.

5. The composition of claim 3 wherein said purified polyclonal IgA is present at a concentration of 5 milligrams in a dose.

6. The composition of claim 3 wherein said purified polyclonal IgA is conjugated to the recombinant J chain by a disulfide linkage.

7. The composition of claim 3 further comprising a pharmacutical excipient.

8. The composition of claim 3 further comprising a buffering agent.

9. The composition of claim 3 wherein said purified IgA-J chain is conjugated to the recombinant secretory component by a disulfide linkage.

* * * * *

UNITED STATES PATENT AND TRADEMARK OFFICE
CERTIFICATE OF CORRECTION

PATENT NO. : 6,932,967 B2  Page 1 of 1
DATED : August 23, 2005
INVENTOR(S) : Michael R. Simon It is certified that error appears in the above-identified patent and that said Letters Patent is hereby corrected as shown below:

Column 1,
Line 33, replace "patent" with -- patients --.
Line 55, replace "etεl." with -- et al., --.

Column 2,
Lines 9 and 12, replace "etal." with -- et al., --.
Line 21, replace "et a." with -- et al., --.

Column 3,
Line 54, replace "cryo-supematant" with -- cryo-supernatant --.

Column 4,
Line 23, replace "Croftet" with -- Crottet --.

Column 5,
Line 10, replace "Weltzin eta.," with -- Weltzin et al., --.

Column 8,
Line 9, replace "purified IgA" with -- purified polyclonal Iga --.

Signed and Sealed this

Twenty-third Day of May, 2006

JON W. DUDAS
*Director of the United States Patent and Trademark Office*